United States Patent
Carden et al.

(10) Patent No.: US 9,505,662 B2
(45) Date of Patent: *Nov. 29, 2016

(54) METHOD FOR COLORING CERAMICS VIA COLLIDAL DISPERSION

(71) Applicant: James R. Glidewell Dental Ceramics, Inc., Newport Beach, CA (US)

(72) Inventors: Robin A. Carden, San Juan Capistrano, CA (US); Thomas C. Valenti, Irvine, CA (US); Frank A. Jimenez, Irvine, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/152,655

(22) Filed: May 12, 2016

(65) Prior Publication Data

US 2016/0251268 A1 Sep. 1, 2016

Related U.S. Application Data

(63) Continuation of application No. 13/410,251, filed on Mar. 1, 2012, now Pat. No. 9,365,459.

(51) Int. Cl.
  *A61K 6/02* (2006.01)
  *C04B 35/626* (2006.01)
  *C04B 35/48* (2006.01)

(52) U.S. Cl.
  CPC ........... *C04B 35/6264* (2013.01); *C04B 35/48* (2013.01); *C04B 2235/3224* (2013.01); *C04B 2235/3241* (2013.01); *C04B 2235/443* (2013.01); *C04B 2235/444* (2013.01); *C04B 2235/445* (2013.01); *C04B 2235/448* (2013.01); *C04B 2235/6027* (2013.01); *C04B 2235/9661* (2013.01)

(58) Field of Classification Search
  CPC .................................................. A61K 6/024
  USPC ............................................ 264/16; 501/134
  See application file for complete search history.

(56) References Cited

U.S. PATENT DOCUMENTS

| | | |
|---|---|---|
| 4,557,691 A | 12/1985 | Martin et al. |
| 6,709,694 B1 | 3/2004 | Suttor et al. |
| 8,865,033 B2 | 10/2014 | Schechner et al. |
| 9,365,459 B2 * | 6/2016 | Carden .................. A61K 6/024 |
| 2002/0081269 A1 | 6/2002 | Trom et al. |
| 2005/0103230 A1 | 5/2005 | Baldi et al. |
| 2008/0303181 A1 | 12/2008 | Holand et al. |
| 2009/0042167 A1 | 2/2009 | Van Der Zel |
| 2010/0062398 A1 | 3/2010 | Schechner et al. |
| 2010/0221683 A1 | 9/2010 | Franke et al. |
| 2011/0151411 A1 | 6/2011 | Schechner et al. |
| 2014/0178834 A1 | 6/2014 | Jahns et al. |

FOREIGN PATENT DOCUMENTS

| | | |
|---|---|---|
| DE | 19619165 | 9/1997 |
| WO | 2010039910 | 4/2010 |

OTHER PUBLICATIONS

International Search Report issued in PCT/US13/27951 dated Jun. 17, 2013.
International Search Report issued in PCT/US13/27961 dated Jun. 28, 2013.

* cited by examiner

*Primary Examiner* — David Sorkin
(74) *Attorney, Agent, or Firm* — Dianne Burkhard

(57) ABSTRACT

In a method of coloring a ceramic material, a coloring solution consisting of metallic salts is introduced to a ceramic slurry. In a slip casting process, a coloring solution consisting of metallic salts is introduced to a ceramic slurry which is cast into green state bodies. A coloring solution that may comprise for example a metallic salt, a solvent, an organic solvent such as derivatives of propylene oxides, and an acid can be introduced to the slip casting process. Such a coloring solution can be added to the slip casting process. In a method, the coloring solution is thoroughly mixed with the ceramic slurry, after which a ceramic body is cast, dried and finally subjected to a sintering process. After final sinter, the resulting ceramic body possesses an innate color that is homogenous throughout its composition. The method is especially useful for coloring zirconia ceramic material used for making dental restorations.

20 Claims, No Drawings

METHOD FOR COLORING CERAMICS VIA COLLIDAL DISPERSION

CROSS-REFERENCE TO RELATED APPLICATIONS

This application is a continuation of, and claims priority to, U.S. patent application Ser. No. 13/410,251, filed Mar. 1, 2012, which is hereby incorporated by reference in its entirety.

FIELD OF INVENTION

The present invention relates to the process in which a color solution consisting of metallic salts is introduced to a ceramic slurry and subsequently slip cast into blocks of predefined dimensions.

BACKGROUND ART

Current techniques for coloring ceramics have limitations due to processing. At present, methods involve dipping a pre-sintered ceramic body into a coloring solution containing metallic salts. Such methods may often result in inhomogeneous coloring on the surface of the ceramic. In addition, the penetration of the coloring solution into the pores of the ceramic is largely affected by the components, composition, and properties of the solution. Depending on the constituents present in the solution, little or no color penetration can result.

Such disadvantages arise when attempting to color a pre-sintered ceramic. This has prompted the need for an alternative method to color a ceramic body. Such a method will remove the need to color a pre-sintered ceramic body and will result in a ceramic with innate color aesthetics that are homogenous throughout the ceramic both internally and on the surface. The present invention relates to creating a colored ceramic during a slip casting process in which a color solution consisting of metallic salts is introduced into the slip and subsequently cast into blocks.

Current methods for coloring ceramic bodies involve dipping a pre-sintered ceramic of final shape into a coloring liquid. These processes require a wide range of soaking times and drying times to ensure uniform and good quality results. After dipping, the ceramic body is dried and sintered, after which the final color is achieved.

The dipping methods currently used depend largely on the capillary action of the coloring liquid and the infiltration of said liquid into ceramic pores. The properties of the coloring liquid, such as composition, concentration, viscosity, pH, surface tension and wetting ability directly influence the performance of the liquid. Should any property not be optimized, undesirable results such as disproportionate coloring or poor penetration of color into the ceramic body may result.

These methods color ceramic bodies after the ceramic has already been processed and fabricated. The coloring agent is added to the ceramic system after initial fabrication of the ceramic. Therefore, the color is not innate to the ceramic.

SUMMARY OF THE INVENTION

The present invention relates to a slip casting process by which a ceramic slurry is cast into green state bodies. It is during this slip casting that a coloring solution consisting of metallic salts is introduced to the slurry and subsequently slip-cast.

A coloring solution may comprise for example a metallic salt, a solvent, an organic solvent such as derivatives of propylene oxides, and an acid can be introduced to the slip casting process.

Such a coloring solution can be added to the slip casting process. The solution is thoroughly mixed with the ceramic slurry, after which the ceramic body is cast, dried and finally subjected to a sintering process.

After final sinter, the resulting ceramic body possesses an innate color that is homogenous throughout its composition.

The present invention utilizes metallic salts as the coloring agent present in the coloring liquid that is added to the slip casting process. The primary property of the metallic salt is such that is soluble in the solvent.

Metallic salts of transition metals from groups 3-12 on the periodic table can be used for the coloring solution. In addition, salts from rare earth metals can be used as well. Metallic salts in the forms of oxides or containing anions such as: $Cl^-$, $SO_4^-$, $SO_3^-$, $Br^-$, $F^-$, $NO_2^-$, and $NO_3^-$ may be used.

The coloring solution, as it relates to the process by which a colored ceramic is made via slip casting, should contain metallic salts in the range of 0.01% to 5% by weight. The concentration of the metallic salts is directly dependent on the target color that is to be achieved.

A preferred coloring solution also contains an organic solvent. The purpose for this solvent is to assure the homogeneity of the solution that contains the metallic salts. Derivatives of polypropylene oxide can be used for this purpose.

The coloring solution, as it relates to the process by which a colored ceramic is made via slip casting, should be comprised of an organic solvent of 1% to about 10% by weight.

A preferred coloring solution also contains acid. The purpose of this component is to maintain the colloidal stability of the coloring solution when mixed into the ceramic slurry by upholding a stable pH. An acidic pH level in the range of 1.0 to 4.0 is ideal.

The coloring solution, as it relates to the process by which a colored ceramic is made via slip casting, should be comprised of an acid of 0.05% to about 5% by weight.

The primary property of the solvent is that it can dissolve the metallic salts and facilitate a homogenous solution. Solvents can include water, alcohols, ketones, organic solvents, or mixtures thereof. The solvent comprises the majority of the solution by weight.

The present invention encompasses the process by which the colored ceramic is fabricated. Due to the unique properties of color that includes hue, chroma and value, varying ratios of coloring liquid are added to the ceramic slurry before the slip casting process. The ratio is directly dependent on the target color that is to be achieved.

The colloidal slip, as it relates to the process by which a colored ceramic is made via slip casting, should have a ratio of grams of coloring liquid per gram of ceramic slurry in a range of about 0.01 to about 1.00.

The present invention may be employed in the fabrication of a colored ceramic using a unique colloidal mixing process of a coloring agent into a ceramic slurry. The coloring liquid is added to the ceramic slurry and afterward mixed to assure that a homogenous mixture is attained. The slurry mixture is then slip cast into preformed molds.

Once slip cast, the ceramic bodies are dried before being subjected to a sintering process. After final sinter, a homogeneously colored ceramic body results.

An object of this invention is to create a ceramic body with a color of specific hue, chroma, and value. A further object is to create a process that allows for a multitude of colors to be achieved.

Still a further object is to create a process that allows for the fabrication of a ceramic body with a homogeneous and uniform color without adverse effects on the mechanical and optical properties of the ceramic.

Still a further object is to create a coloring solution designed for the ceramic fabrication process that results in a uniformly colored ceramic.

DETAILED DESCRIPTION

The present invention relates to color a ceramic body during the initial process and fabrication of the ceramic. A coloring solution is added to the ceramic system during the processing stage. The result is a ceramic with intrinsic color properties and complete color saturation.

A color solution of known compositions and concentrations can be used to create any color of desired hue, chroma and value. Using metallic salts as the coloring agent, as well as a solvent to disperse the salts into solution, this invention relates to a process that is designed for coloring a ceramic during the manufacturing process of the material.

The process hereof ensures total and homogeneous color penetration into a ceramic body. Such a ceramic body can then be cut or milled into any shape or form. The final sintered ceramic body will be colored completely without the need for an extra coloring process that normally takes hours using conventional ceramic color methods.

The coloring solution and process hereof do not adversely affect the mechanical and optical properties of the natural ceramic. Because the coloring agent is mixed in a colloidal process, the coloring ions are homogenously distributed through the ceramic's crystal structure. Therefore, the coloring ions are incorporated throughout the ceramic.

The present invention relates to the fabrication of a colored ceramic using a unique colloidal mixing process of a coloring agent into a ceramic slurry. Such a process can be applied to the dental industry, particularly in the fabrication of dental zirconia. At present, zirconia blocks are fabricated for the milling of dental crowns, bridges and copings. Due to the natural strength and aesthetics of teeth, such mechanical and optical properties are needed in dental ceramics.

At present, dental frameworks are milled from zirconia blocks. Because the natural color of zirconia is white, there is a need to color the ceramic. The ceramic is therefore colored using conventional dipping methods using coloring liquids. Current methods involve dipping a pre-sintered zirconia framework of final shape into the color liquid for a specified soaking time period. Frameworks are subsequently dried and sintered. The dental industry at large uses the VITA classic shade guide as a standard for teeth aesthetics. These colors are unique in hue, chroma and value. Conventional color liquids are made to match these properties.

The present invention can eliminate the need for the coloring process of the pre-sintered dental frameworks. A zirconia dental ceramic can be fabricated with the innate color properties of the final desired product.

It is within the scope of the present invention to fabricate a dental zirconia ceramic with a color that matches the hue, chroma and value of the VITA Classic dental shades.

It is also within the scope of the present invention to fabricate a dental zirconia ceramic block that can be milled to a specified dental framework of final shape and subsequently sintered. The resulting sintered zirconia framework will be of final shape and color that matches the VITA Classic shades.

Testing Results

Successful results have been achieved with the present invention. A coloring solution of known concentration and composition and mixed it into a colloidal zirconia slurry was used.

A coloring solution containing $TbCl_3$, $CrCl_3$, propylene glycol, 37% hydrochloric acid and de-ionized water was added to a zirconia slurry.

The exact composition of the coloring solution is as follows: 0.0914 wt % $TbCl_3$, 0.0609 wt % $CrCl_3$, 2.070 wt % propylene glycol, and 0.104 wt % hydrochloric acid. The balance was de-ionized water. The final pH of the solution was measured to be 1.93.

A ratio of 0.0218 grams of coloring liquid per gram of zirconia slurry was blended into a homogeneous mixture.

The slurry was subsequently slip cast into a disc shape and dried. This was followed by a sintering process during which the discs were fired into a pre-sintered bisque stage. After final sinter, the colored ceramic was cut to assure complete color saturation.

Total and homogenous coloring of the ceramic block was achieved. Using a VITA Easyshade instrument, the color was checked to verify if a dental shade had indeed been matched. The final color matched closely to the VITA Classic shade B2.

A second test was performed to verify the results of the first. A coloring liquid of different composition and concentration was used for processing.

The exact composition of the coloring solution is as follows: 0.122 wt % $TbCl_3$, 0.081 wt % $CrCl_3$, 2.030 wt % propylene glycol, and 0.104 wt % hydrochloric acid. The balance was de-ionized water. The final pH of the solution was measured to be 1.96.

A ratio of 0.0218 grams of coloring liquid per gram of zirconia slurry was blended into a homogeneous mixture.

The slurry was subsequently slip cast into a disc shape and dried. This was followed by a sintering process during which the discs were fired into a pre-sintered bisque stage. After final sinter, the colored ceramic was cut to assure complete color saturation.

Total and homogenous coloring of the ceramic block was achieved. Using a VITA Easyshade instrument, the color was checked to verify if dental shade had indeed been matched. The final color matched closely to the VITA Classic shade A1.

Therefore, it will be understood that the present invention, as it relates to a coloring liquid that is introduced to a colloidal process by which a colored ceramic is fabricated, has proven to be particularly useful in the dental industry to create a dental ceramic with intrinsic colors that match the desired aesthetics of dental frameworks.

It will now be appreciated that the present invention relates to a unique process for providing selected coloring of ceramic materials in slip cast fabrication by introducing a coloring solution of metallic salts into the slurry. This invention is particularly applicable to the coloring of slip cast fabricated zirconia blocks for use as dental restorations such as full contour crowns, bridges and the like. While exemplary embodiments have been disclosed herein, the scope hereof will be limited only by the appended claims and their legal equivalents.

The invention claimed is:

1. A method of making a colored zirconia ceramic body comprising;

a) obtaining a coloring solution consisting essentially of 0.01% to 5% by weight of at least one metallic salt by weight of the coloring solution, a solvent, and optionally, an acid, wherein the at least one metallic salt is soluble in the solvent;
b) choosing an amount of the coloring solution and an amount of a zirconia ceramic slurry in a ratio of about 0.01 gram to about 1.00 gram coloring solution per gram of zirconia ceramic slurry to provide a selected hue, chroma, and value to a colored zirconia ceramic body;
c) adding the amount of the coloring solution to the amount of a zirconia ceramic slurry;
d) mixing to distribute the coloring solution throughout the zirconia ceramic slurry to form a colored zirconia slurry; and
e) slip-casting the colored zirconia slurry to form a colored zirconia ceramic body made predominantly of zirconia.

2. The method of claim 1, wherein the at least one metallic salt is selected from transition metals from group 3-12 of the periodic table.

3. The method of claim 1, wherein the at least one metallic salt is selected from rare earth metals.

4. The method of claim 1, wherein the at least one metallic salt contains anions.

5. The method of claim 1, wherein the at least one metallic salt contains anions selected from $Cl^-$, $SO_4^-$, $SO_3^-$, $Br^-$, $F^-$, $NO_2^-$, and $NO_3^-$.

6. The method of claim 1, wherein the at least one metallic salt is $TbCl_3$ and $CrCl_3$.

7. The method of claim 1, wherein the solvent is selected from water, an organic solvent, or mixtures thereof.

8. The method of claim 1, further comprising firing the colored zirconia ceramic body to a bisque stage.

9. The method of claim 1, wherein step b) comprises choosing an amount of the coloring solution and an amount of a zirconia ceramic slurry in a ratio to provide a selected hue, chroma, and value of a dental shade in a final sintered product made from the colored zirconia ceramic body.

10. The method of claim 1, wherein a final sintered ceramic body made by sintering the colored zirconia ceramic body comprises color penetration throughout the final sintered ceramic body.

11. A method of coloring a zirconia ceramic comprising;
a) obtaining a coloring solution consisting essentially of at least one metallic salt selected from transition metals from groups 3-12 of the periodic table and rare earth metals, and a solvent, and optionally, an acid, wherein the at least one metallic salt is soluble in the solvent;
b) choosing an amount of the coloring solution and an amount of a zirconia ceramic slurry in a ratio of about 0.01 gram to about 1.00 gram coloring solution per gram of the zirconia ceramic slurry to provide a selected hue, chroma, and value to a colored zirconia ceramic body;
c) adding the amount of coloring solution to the amount of a zirconia ceramic slurry; and
d) mixing to distribute the coloring solution throughout the zirconia ceramic slurry to form a colored zirconia slurry that may be slip cast to form a colored zirconia ceramic body.

12. The method recited in claim 11, wherein in step a) the coloring solution contains an acid.

13. The method recited in claim 12, wherein in step a) the acid comprises 0.05% to 5% by weight of the coloring solution.

14. The method recited in claim 11, wherein in step a) the solvent is selected from water, alcohols, ketones, organic solvents, and mixtures thereof.

15. The method recited in claim 11, wherein the solvent comprises a derivative of a propylene oxide.

16. The method of claim 11, wherein the at least one metallic salt comprises 0.01% to 5% by weight of the coloring solution.

17. The method of claim 11, wherein the at least one metallic salt comprises 0.01% to 5% by weight of the coloring solution and the coloring solution comprises $TbCl_3$ and $CrCl_3$.

18. The method of claim 11, further comprising slip casting the colored zirconia ceramic slurry to form a colored zirconia ceramic body that is predominantly zirconia.

19. The method of claim 18, further comprising firing the colored zirconia ceramic body to a bisque stage.

20. The method of claim 18, wherein step b) comprises choosing an amount of the coloring solution and an amount of a zirconia ceramic slurry in a ratio to provide a selected hue, chroma, and value of a dental shade in a final sintered product made from the colored zirconia ceramic body.

* * * * *